United States Patent
Williams et al.

(10) Patent No.: US 10,927,050 B2
(45) Date of Patent: Feb. 23, 2021

(54) MULTI-STRAND PLANT AND PROCESS FOR PRODUCING OLEFINS FROM OXYGENATES

(71) Applicant: L'Air Liquide, Société Anonyme pour l'Etude et l'Exploitation des Procédés Georges Claude, Paris (FR)

(72) Inventors: Bryce Williams, Frankfurt am Main (DE); Stephane Haag, Frankfurt am Main (DE); Christopher Drosdzol, Frankfurt am Main (DE); Frank Castillo-Welter, Friedrichdorf (DE)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 16/873,554

(22) Filed: May 1, 2020

(65) Prior Publication Data
US 2020/0346994 A1  Nov. 5, 2020

(30) Foreign Application Priority Data
May 3, 2019  (EP) .................................... 19020320

(51) Int. Cl.
*C07C 1/20* (2006.01)
*B01J 19/24* (2006.01)
*B01J 8/04* (2006.01)

(52) U.S. Cl.
CPC ............... *C07C 1/20* (2013.01); *B01J 8/0492* (2013.01); *B01J 8/0496* (2013.01);
(Continued)

(58) Field of Classification Search
CPC .. C07C 1/20; C07C 11/02; C07C 4/06; C07C 11/06; C07C 41/09; C07C 2529/40;
(Continued)

(56) References Cited

U.S. PATENT DOCUMENTS

| 4,404,414 A | 9/1983 | Penick et al. |
| 8,444,940 B2 * | 5/2013 | Bach ................. B01J 8/0496 422/618 |

(Continued)

FOREIGN PATENT DOCUMENTS

| DE | 10 2014 112 792 | 3/2016 |
| WO | WO 03 051510 | 6/2003 |
| WO | WO 2007 140844 | 12/2007 |

OTHER PUBLICATIONS

European Search Report for corresponding EP 19020320.8, dated Nov. 1, 2019.

*Primary Examiner* — Sharon Pregler
(74) *Attorney, Agent, or Firm* — Elwood L. Haynes

(57) ABSTRACT

The invention relates to a multi-strand plant and a corresponding process for producing olefins from oxygenates in which a plurality of reactor trains which each comprise one or more catalyst-containing oxygenate-to-olefin (OTO) reaction zones are arranged in parallel and operated in parallel, wherein at least one of the parallel reaction zones may be operated in a regeneration mode while the OTO synthesis reaction may be performed in the other reaction zones parallel thereto. The partial product streams obtained from the individual reactor trains operated in a synthesis mode are discharged via partial product conduits, combined into a complete product conduit using a connecting device, compressed using a compressor and separated into a plurality of olefin-containing hydrocarbon fractions using a multi-stage workup apparatus. The inventive configuration of the plant and of the process reduces pressure drops and thus enhances the yield for short-chain olefins, for example propylene.

15 Claims, 5 Drawing Sheets

(52) U.S. Cl.
CPC .. B01J 19/2445 (2013.01); *B01J 2208/00106* (2013.01); *C07C 2529/06* (2013.01)

(58) Field of Classification Search
CPC ... C07C 11/08; C07C 43/043; C07C 2521/04; C07C 2529/70; C07C 41/01; C07C 2529/85; B01J 2219/00006; B01J 8/0453; B01J 8/0492; B01J 29/90; B01J 19/24; B01J 19/245; B01J 19/26; B01J 19/30; B01J 19/32; B01J 29/40; B01J 38/14; B01J 4/002; B01J 8/005; B01J 8/0242; B01J 8/0285; B01J 8/0496; B01J 38/02; B01J 38/32

See application file for complete search history.

(56) References Cited

U.S. PATENT DOCUMENTS

| | | |
|---|---|---|
| 10,214,461 B2 * | 2/2019 | Rothamel ............... C07C 41/01 |
| 2005/0085375 A1 | 4/2005 | Bach et al. |
| 2006/0161035 A1 * | 7/2006 | Kalnes ..................... C07C 6/04 585/639 |
| 2010/0063337 A1 | 3/2010 | Bach et al. |
| 2011/0021857 A1 | 1/2011 | Cao et al. |
| 2015/0299067 A1 * | 10/2015 | Kloth ....................... C07C 4/06 585/302 |
| 2016/0068452 A1 | 3/2016 | Rothamel et al. |

* cited by examiner

MULTI-STRAND PLANT AND PROCESS FOR PRODUCING OLEFINS FROM OXYGENATES

CROSS REFERENCE TO RELATED APPLICATIONS

This application claims the benefit of priority under 35 U.S.C. § 119 (a) and (b) to European Patent Application No. EP 19020320.8, filed May 3, 2019, the entire contents of which are incorporated herein by reference.

BACKGROUND

Field of the Invention

The invention relates to a multi-strand plant for producing olefins from oxygenates in which a plurality of reactor trains which each comprise one or more catalyst-containing oxygenate-to-olefin (OTO) reaction zones are arranged in parallel and operated in parallel. Precautions are taken to ensure that at least one of the parallel reaction zones may be operated in a regeneration mode while the OTO synthesis reaction may be performed in the other reaction zones parallel thereto. The partial product streams obtained from the individual reactor trains operated in a synthesis mode are discharged via partial product conduits, combined into a complete product conduit using a connecting device, compressed using a compressor and separated into a plurality of olefin-containing hydrocarbon fractions using a multi-stage workup apparatus.

The invention further relates to a process for producing olefins from oxygenates using a corresponding plant.

Prior Art

Short-chain olefins, especially propylene (propene) and ethylene (ethene), are among the most important commodities in the chemical industry. The reason for this is that, proceeding from these unsaturated compounds with a short chain length, it is possible to form molecules having a long-chain carbon skeleton and additional functionalizations.

The main source of short-chain olefins in the past was steamcracking, i.e. thermal cracking of hydrocarbon fractions comprising essentially saturated hydrocarbons in mineral oil processing. In the past few years, however, further processes for preparing short-chain olefins have been developed. One reason for this is rising demand that can no longer be covered by the available sources; secondly, the increasing scarcity of fossil raw materials is requiring the use of different starting materials.

The so-called MTP (methanol-to-propylene) or else MTO (methanol-to-olefin) processes for preparing propylene and other short-chain olefins proceed from methanol as starting material. These heterogeneously catalyzed processes comprise initially partially forming from methanol the intermediate product dimethyl ether (DME) and from a mixture of methanol and dimethyl ether then subsequently forming in an olefin synthesis reactor using a shape-selective, zeolite-based or molecular sieve-based solid catalyst a product mixture of ethylene, propylene and the isomeric butenes as short-chain olefins and also heavier hydrocarbons with more than four carbon atoms. The product stream also contains water which derives not only from the process steam which is optionally supplied to the MTO reactor as a dilution medium but also from the water of reaction produced in the synthesis reactor.

Since in addition to methanol and DME other short-chain, oxygen-containing organic molecules, for example alcohols other than methanol, may be used as inputs, it is customary also to refer more generally to oxygenate-to-olefin reactions (OTO reactions) and oxygenate-to-olefin syntheses (OTO syntheses).

Due to the high exothermicity of the reactions proceeding during OTO synthesis which can result in unwanted byproducts and premature catalyst aging/deactivation it is preferred when using fixed bed reactors to arrange the solid, granular or chunk-form OTO synthesis catalyst in individual catalysts zones, catalyst layers or catalyst trays between which an intermediate cooling, for example by introduction of cold input gas/reactant gas, may be effected. One possible configuration of such a reactor is shown in international patent application WO 2007/140844 A1.

The subsequent purification of the product stream from the synthesis reactor is intended to separate unwanted byproducts and unconverted reactants and also to produce the individual hydrocarbon fractions in the highest possible purity. To this end it is customary to employ in the first step a quench system in order through intensive and rapid contacting to bring about an immediate cooling of the product stream from the synthesis reactor by direct heat exchange with a fluid, usually liquid, quenching medium, for example water. One desired side effect of this is a certain gas scrubbing effect on the product stream which is typically at least partially in the form of a gas or vapour.

One example of the workup of the synthesis reactor product stream which follows an OTO reaction may be found in DE 10 2014 112 792 A1, which describes how in a first step a heterogeneously catalysed conversion of at least one oxygenate to afford a product stream containing C2 olefins, C3 olefins, C4 olefins, C5/6 hydrocarbon compounds and C7+ hydrocarbon compounds, and in a second step a separation of a propylene stream consisting to an extent of at least 95% by weight of C3 olefins, is achieved.

The further workup units described in DE 10 2014 112 792 A1 are in accordance with the concept customary in the art. The quenching may already bring about a coarse separation of the fractions according to their chain length of the resultant olefins due to partial condensation, thus allowing a liquid C4+ fraction to be discharged from the quench. The C4− fraction separated in gaseous form is subsequently introduced into a compression stage. The C4− fraction from the compression is then sent to a separation apparatus in which C3− hydrocarbons are separated from the C4+ hydrocarbons. In subsequent purifying steps the C3 fraction is separated from the C2− fraction in a further separating unit, wherein this has to be carried out under pressure owing to the low boiling points of the two fractions.

When performing the OTO synthesis reaction over solid zeolite-based catalysts it must be noted that—similarly to other hydrocarbon conversion reactions using such reactions, for example catalytic olefin cracking—a continuous and comparatively rapid deactivation of the catalyst takes place which is correlated with the blocking and/or occupying of active catalytic sites by carbonaceous solid deposits. This deactivation phenomenon therefore also referred to as coking may be largely reversed by oxidative removal of the deposits, i.e. by targeted burnoff. The reaction conditions required therefor are for example taught for the case of a zeolite catalyst deactivated during catalytic olefin cracking in international patent application WO 2003/051510 A2. The regenerant employed is often an oxygen-containing gas stream, for example an air stream diluted with nitrogen and/or steam, wherein the oxygen content of the regenerant, the treatment temperature or both parameters are increased in stepwise fashion to achieve the most complete possible removal of the carbonaceous deposits.

The reactivation of a catalyst deactivated during an OTO synthesis is described in patent publication US 2011/0021857 A1. Since this document relates to a process with a moving catalyst it is possible to transfer the deactivated catalyst from a reaction or synthesis stage into a regeneration stage, to carry out the regeneration there and subsequently to return the regenerated catalyst to the synthesis stage.

However, in order to be able to carry out such a reactivation in synthesis reactors which contain a solid catalyst, for example in the form of a fixed dumped bed, it is necessary to separate the corresponding reactor/reactor train from the oxygenates-containing reactant stream in order to be able to carry out the oxidative decoking. Avoiding shutdown of the entire olefin production plant may therefore be achieved with a multi-strand configuration thereof in which a plurality of reactor trains each comprising one or more catalyst-containing oxygenate-to-olefin (OTO) reaction zones are arranged in parallel and operated in parallel and in which at least one of the parallel reaction zones is in a regeneration mode while the OTO synthesis reaction continues to be operated in the other reaction zones parallel thereto. This ensures continuous olefin production and the plants and process stages downstream of the reactor trains may likewise be operated continuously. It is important here to safely separate the reactor trains in regeneration mode from the reactor trains in synthesis mode in order to avoid unintended mixing of the usually oxygen-containing regeneration medium with hydrocarbon-containing input or product streams to form flammable or even explosive gas mixtures.

A further important aspect in OTO synthesis is the reaction pressure. OTO synthesis is generally used to produce hydrocarbons normally containing more carbon atoms than the oxygenates used as reactants such as methanol or dimethyl ether (DME). Due to the liberation of steam as a byproduct these reactions are accompanied by an increase in volume. This is elucidated by way of example herein-below by the gross reaction equations for the formation of ethylene from methanol/DME $$2\ CH_3OH = C_2H_4 + 2\ H_2O$$

$$CH_3(O)CH_3 = C_2H_4 + H_2O$$

To achieve high olefin yields it is therefore preferable to perform the OTO synthesis at the lowest possible reaction pressure.

In summary it may therefore be concluded that there remains a need for improved olefin synthesis processes which make it possible to realize continuous olefin production coupled with high olefin yield.

SUMMARY

The present invention accordingly has for its object to provide a corresponding improved plant for continuous production of olefins from an oxygenates-containing fluid input mixture and a corresponding process.

This problem is substantially solved by a plant having the features of claim 1 and by a plant having the features of claim 13. Further, especially preferred, embodiments of the process according to the invention and the plant according to the invention may be found in the subsidiary claims of the respective category.

In the context of the present invention workup steps, purification steps or separation steps are in principle to be understood as meaning all process steps that make use of a thermal separation process, preference being given to using distillation or rectification. The same applies to the apparatuses and plants associated with the performance of these steps.

Fluid connection between two regions or plant components is to be understood here as meaning any kind of connection that enables flow of a fluid, for example a reaction product or a hydrocarbon fraction, from one to the other of the two regions, irrespective of any interposed regions, components or required conveying means. A fluid or fluid medium is to be understood as meaning substances which continuously deform, i.e. flow, under the influence of shear forces. These are in particular gases and liquids, but also multi-phase liquid-liquid mixtures and gas-liquid mixtures, for example gas flows with an entrained condensate fraction or aerosols.

A means is to be understood as meaning something that enables or is helpful in the achievement of a goal. In particular, means for performing a particular process step are to be understood as including all physical articles that would be considered by a person skilled in the art in order to be able to perform this process step. For example, a person skilled in the art will consider means of introducing or discharging a material stream to include all transporting and conveying apparatuses, i.e. for example pipelines, pumps, compressors, valves, which seem necessary or sensible to said skilled person for performance of this process step on the basis of his knowledge of the art.

Oxygenates are in principle to be understood as meaning all oxygen-containing hydrocarbon compounds that may be converted under oxygenate conversion conditions into olefins, especially into short-chain olefins such as propylene, and further hydrocarbon products. Examples of suitable oxygenate conversion conditions are known to those skilled in the art or may be found in the relevant literature, for example the patent publications recited at the outset.

Short-chain hydrocarbons in the context of the present invention are especially to be understood as meaning hydrocarbons that are gaseous under ambient conditions, for example, in the case of olefins, ethylene, propylene and the isomeric butenes 1-butene, cis-2-butene, trans-2-butene, isobutene.

Higher hydrocarbons in the context of the present invention are especially to be understood as meaning hydrocarbons that are liquid under ambient conditions.

The recited solid, liquid and gaseous/vaporous states of matter should always be considered in relation to the local physical conditions prevailing in the respective process step or in the respective plant component unless otherwise stated. In the context of the present application the gaseous and vaporous states of matter should be considered to be synonymous. The term "vaporous" is merely used to illustrate that the particular substance is normally liquid under ambient conditions.

In the context of the present invention separating a material stream is to be understood as meaning separation of the stream into at least two substreams. Unless otherwise stated it may be assumed that the physical composition of the substreams corresponds to that of the starting stream except in cases where it is immediately apparent to a person skilled in the art that there must inevitably be a change in the physical composition of the substreams owing to the separation conditions, as is the case for distillation for example.

A heat transfer relationship is to be understood as meaning the presence of heat exchange between two regions, wherein all mechanisms of direct or indirect heat exchange such as thermal conduction, convection or radiation may be involved and wherein the regions concerned need not be directly adjacent but may also be separated through walls or intermediate regions.

The predominant portion of a fraction, of a material stream etc. is to be understood as meaning a proportion quantitatively greater than all other proportions each considered alone. Especially in the case of binary mixtures or in the case of separation of a fraction into two parts, this is understood to mean a proportion of more than 50% by weight, unless otherwise stated in the specific case.

The indication that a material stream consists predominantly of one component or group of components is to be understood as meaning that the mole fraction or mass fraction of this component or component group is quantitatively greater than all other proportions of other components or component groups in the material stream each considered alone. Especially in the case of binary mixtures this is to be understood as meaning a proportion of more than 50%. Unless otherwise stated in the specific case this is based on the mass fraction.

Pressures are reported in bar, absolute, bar(a) for short, or pascals, absolute, Pa(a) for short, unless otherwise stated in the particular context.

The invention is based on the realization that to achieve high target product yields for short-chain olefins such as ethylene or propylene it is important to keep the pressure level in the reaction zones as low as possible on account of the above-mentioned pressure dependence of the olefin synthesis reactions. Since performing the reaction under reduced pressure/partial vacuum is too costly and complex and thus uneconomic, reaction at or near atmospheric pressure is most suitable. However, in practice pressure drops over conduit paths and interposed components must always be taken into account and therefore a certain positive pressure in the reaction zones is unavoidable in order to achieve a sufficient reactor throughput. In order to minimize this positive pressure it is especially important to reduce the pressure drops in the conduit paths downstream of the reaction zones right up to the compressor since the sum of the pressure drops defines the minimum pressure level of the reactor and of the reaction zones present. Thus the sooner after leaving the reaction zones a pressure reduction may be brought about, the more positive an effect this reduction will have on the pressure level in the reaction zones. It is therefore advantageous to provide a thermal recovery apparatus in each of the individual parallel reactor trains immediately downstream of the reaction zones even if this markedly increases capital costs compared to a plant with a common thermal recovery apparatus for all reactor trains. The volume reduction brought about by temperature reduction reduces the pressure already immediately downstream of the reaction zones. This is intensified by the arrangement of a first quench zone downstream of the thermal recovery apparatus and upstream of the compressor since this brings about a marked cooling by means of which the water proportion of the product stream(s) is largely or even entirely condensed. As mentioned at the outset the product stream contains water which derives not only from the process steam which is optionally supplied to the OTO reactor as a dilution medium but also from the water of reaction produced in the synthesis reactor. Condensation of this water content therefore results in a marked volume and thus pressure reduction.

As mentioned hereinabove when operating multi-strand hydrocarbon synthesis plants in which one or more of the reactor trains are in regeneration mode while the hydrocarbon synthesis is operated in other reactor trains in parallel therewith it is particularly important to undertake safe separation or shutoff of the reactor trains operated in the different operating modes to avoid unintended mixing of the usually oxygen-containing regeneration medium with hydrocarbon-containing input or product streams to form flammable or even explosive gas mixtures. According to the invention this is achieved by the provision of shutoff devices in the conduit path of the partial product conduits for separation of the reactor train from downstream plant parts and parallel reactor trains. Shutoff devices that may be employed are the apparatuses known to those skilled in the art, i.e. for example valves, sliders, throttle flaps or spade blinds. The introduction of a shutoff device into the conduit path of a partial product conduit generally results in a further increase in the pressure drop, the magnitude of which may vary depending on the type of the shutoff device. It is therefore all the more important to very largely reduce the pressure drops in the conduit paths downstream of the reaction zones right up to the compressor.

A preferred embodiment of the plant according to the invention is characterized in that arranged in every reactor train downstream of the thermal recovery apparatus are at least two partial product conduits for discharging the partial product stream from the reactor train which are arranged in parallel and operable in parallel, wherein at least one shutoff device is present in the conduit path of each of the parallel partial product conduits. This allows efficient reduction of the pressure drop in this conduit section. The advantage of using at least two, preferably two, partial product conduits arranged in parallel and operable in parallel which each have at least one, preferably one, shutoff device is that it is possible to employ as shutoff devices for example valves having a relatively small internal diameter which have a lower leakage rate than valves having a relatively large internal diameter.

Valves having an internal diameter of about 60 inches are normally the largest commercially available standard-size valves. Valve choice represents a compromise between the size, cost and ability of the valve to prevent leakage when in the closed position after repeated switching cycles. In general, larger valves have a higher leakage rate and are more costly. An advantageous compromise between costs and performance is achieved by a valve diameter of about 40 inches.

Valves are typically specified according to the desired pressure drop. In the present situation it is desirable to have the lowest possible pressure drop in the open position. While many valve types may be employed the requirement for the lowest possible pressure drop naturally leads to a preferred choice of valves of the type having a throttle or shutoff flap for example. Even then, the actual pressure drop depends on the fluid flow rate passing through the valve and the attached pipelines.

In order to achieve a particularly safe isolation between the oxygen-containing regenerant and the hydrocarbon-containing product stream it is advantageous to use two valves arranged in series. The leakage rate of two valves in series is significantly further reduced compared to a single valve and it is also possible to decompress the space between the two valves and vent it to a safe location or fill it with an inert gas such as nitrogen when the corresponding reactor train is to be operated in regeneration mode. This allows a particularly safe separation of the reactor trains that are in synthesis mode and in regeneration mode respectively. However, this makes it all the more important that each of the valves arranged in series exhibits the lowest possible pressure drop.

It is especially preferable having regard to the plant according to the invention that a first quench zone for performing direct heat exchange between a partial product stream and a first quenching medium is comprised and is arranged downstream of the thermal recovery apparatus and upstream of the connecting device, i.e. still in the partial product conduits, and that a second quench zone for performing direct heat exchange between the complete product stream and a second quenching medium is further comprised and is arranged downstream of the connecting device and upstream of the compressor, i.e. in the complete product conduit, and is in fluid connection with all partial product conduits from the individual reactor trains. This brings about a further pressure reduction still in the partial product conduits which is added to the pressure reduction effected by the thermal recovery apparatuses. The pressure reduction effected by the first quench zone is particularly large if it is operated such that the steam present in the partial product streams is very largely, preferably almost completely, condensed. Since—depending on the use of steam as a moderator in OTO synthesis—the partial product streams based on mole fractions may consist predominantly of steam and this is additionally supplemented by water formed as a byproduct in the synthesis reactions the extensive condensation of the water content of the partial product streams achieves a particularly marked volume reduction and thus a particularly pronounced pressure reduction. The second quench zone arranged in the complete product conduit may then further advantageously be configured and operated such that condensable/absorbable hydrocarbons may be separated therein specifically. This achieves a further pressure reduction and the separated hydrocarbons may be supplied to the workup apparatus specifically, wherein due to the preseparation of the water in the first quench zone the volume flow of the liquid stream that is now to be treated, for example in a liquid-liquid phase separation, is markedly reduced. The corresponding apparatuses can therefore be made smaller thus resulting in capital cost savings.

Having regard to the last-mentioned embodiment it is preferable when the first quench zone is arranged downstream of the thermal recovery apparatus and upstream of the shutoff device. As explained hereinabove a particularly marked pressure reduction is achieved when the first quench zone used for water separation is arranged still in the partial product conduits.

A further preferred embodiment of the plant according to the invention is characterized in that the at least one reaction zone and the thermal recovery apparatus arranged downstream of the reaction zone are arranged in a common vessel, wherein the partial product conduit arranged downstream of the thermal recovery apparatus is used to discharge the partial product stream from the vessel. The arrangement of the reaction zone and the thermal recovery apparatus in a common vessel obviates the need for the connecting conduit between these plant parts and a further pressure reduction is achieved since the conduit cross section of the connecting conduit is generally smaller, and the pressure drop per unit length higher, than for the common vessel.

In a further aspect of the invention the plant is characterized in that
the at least one reaction zone and the thermal recovery apparatus arranged downstream of the reaction zone are arranged in a common vessel,
the partial product stream is discharged from the vessel using the partial product conduit arranged downstream of the thermal recovery apparatus,
all partial product conduits of the reactor trains are combined using the connecting device,
the first quench zone is arranged between the connecting device and the compressor and is in fluid connection with all partial product conduits of the individual reactor trains.

The abovementioned advantages are retained for the arrangement of a plurality of plant parts in a common vessel. A particularly effective pressure reduction is achieved in combination with the other features of this embodiment.

In a further aspect the plant according to the invention is characterized in that
the at least one reaction zone, the thermal recovery apparatus arranged downstream of the reaction zone and the first quench zone arranged downstream of the thermal recovery apparatus are arranged in a common vessel,
the partial product stream is discharged from the vessel using the partial product conduit arranged downstream of the first quench zone,
all partial product conduits of the reactor trains are combined using the connecting device,
the second quench zone is arranged between the connecting device and the compressor and is in fluid connection with all partial product conduits of the individual reactor trains.

The abovementioned advantages are retained for the arrangement of a plurality of plant parts in a common vessel. A particularly effective pressure reduction is achieved in combination with the other features of this embodiment.

In a further aspect the plant according to the invention is characterized in that the at least one reaction zone, the thermal recovery apparatus arranged downstream of the reaction zone, the first quench zone arranged downstream of the thermal recovery apparatus and the second quench zone arranged downstream of the first quench zone are arranged in a common vessel,
the partial product stream is discharged from the vessel using the partial product conduit arranged downstream of the second quench zone,
all partial product conduits of the reactor trains are combined using the connecting device.

The abovementioned advantages are retained for the arrangement of a plurality of plant parts in a common vessel. A particularly effective pressure reduction is achieved in combination with the other features of this embodiment.

Having regard to the embodiments of the plant according to the invention having a common vessel it is preferable when the common vessel is connected to a conduit for discharging a liquid condensate. The abovementioned advantages are retained for the arrangement of a plurality of plant parts in a common vessel. If condensate separation already occurs in the thermal recovery apparatus it is advantageous to discharge the condensate via the conduit for discharging said condensate since a gas/liquid biphasic flow can result in fluctuations in plant operation on account of pressure variations, entrainment effects and the like. The same applies to an even greater extent to embodiments having one or more quench zones likewise arranged in the common vessel since this necessarily generates a liquid phase that must be discharged from the common vessel.

Having regard to the embodiments of the plant according to the invention having a common vessel it is further preferable when the thermal recovery apparatuses are in the form of plate heat exchangers. Plate heat exchangers have a simple construction, are insensitive to blockages, have good heat transfer properties and bring about only a small pressure drop per unit length and therefore combine advantageously with the other embodiment features likewise directed to reducing the pressure drop.

In a further aspect the last-mentioned embodiment of the plant according to the invention is characterized in that the thermal recovery apparatuses comprise at least two plate heat exchangers operated with different cooling fluids. This makes it possible to achieve particularly effective heat removal analogously to a countercurrent heat exchanger. Employable cooling fluids include cold process media and/or dedicated cooling media. When a cold process medium, for example the oxygenate-containing input stream, is employed in the first cooling step and a further cooling medium is employed in the second cooling step the heating of the process medium may be carried out to the desired temperature for its subsequent use and limited thereto since the remaining cooling is carried out in the second cooling step.

In a further aspect the embodiments of the plant according to the invention having a common vessel are characterized in that the reaction zones are in a heat transfer relationship with plate heat exchangers by means of which the reaction zones are cooled with a cooling fluid by indirect heat exchange. The overall thermal balance of the reactions proceeding during OTO synthesis is strongly exothermic. It is therefore important to remove the heat liberated especially at the catalyst rapidly and near to the site of liberation in order to avoid damage and premature and possibly reversible deactivation of the catalyst. This is achieved by these embodiments.

A preferred embodiment of the process according to the invention is characterized in that the plant comprises three reactor trains, of which two are supplied with oxygenates-containing, fluid input mixture and in parallel thereto one is supplied with a gaseous oxygen-containing regenerant. Studies have shown that based on plant size and the accompanying capital costs this arrangement ensures economically advantageous and continuous olefin production. As soon as regeneration in one reactor train has been completed it is once again available for olefin production and one of the further reactor trains may be switched over into regeneration mode as soon as the activity of the obtained catalyst falls below a minimum level. Thus two reactor trains are available for olefin production at any point in time and the downstream plant parts may be operated continuously which is important especially for the workup apparatus since due to the multiplicity of individual separating operations and apparatuses said apparatus requires a long time to reach a steady state during which time no on-specification products can be produced.

In a further aspect the process according to the invention is characterized in that at least 40%, preferably at least 70%, of the product gas is separated as condensate upstream of the shutoff apparatus. Studies have shown that a separation rate of at least 70% of the product gas as condensate, especially as water, brings about a particularly marked pressure reduction, an elevated propylene yield and relieves the volume load on the downstream plant parts. By contrast a separation rate of at least 40% of the product gas represents an advantageous compromise between the abovementioned advantages on the one hand and the separation effort reflected in the form of required heat exchanger area and coolant requirement on the other hand.

Further features, advantages and possible applications of the invention are apparent from the following description of working examples and the drawings. All the features described and/or depicted, on their own or in any combination, form the subject-matter of the invention, irrespective of their combination in the claims or their dependency references.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DETAILED DESCRIPTION OF PREFERRED EMBODIMENTS

Figure 1:
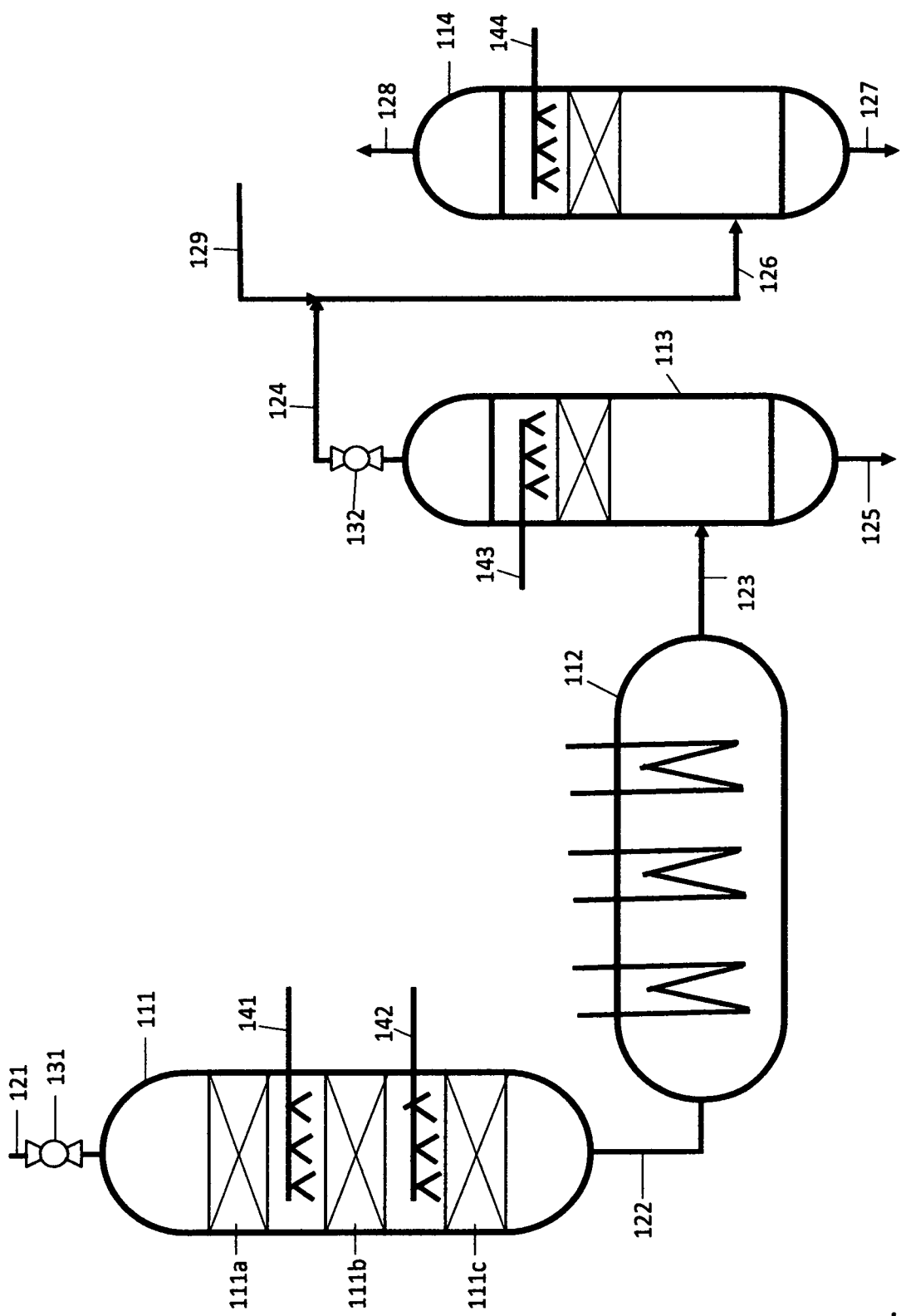
FIG. 1 shows a schematic representation of a first embodiment.

FIG. 1 shows a schematic construction of a reactor train according to a first embodiment of the invention. The reactor train includes the OTO reaction zone 111, a thermal recovery apparatus 112 and a first quench zone 113. The apparatuses are connected to one another via the conduits 122 and 123. A second quench zone 114 is utilized in common by a plurality of reactor trains arranged in parallel as indicated by conduit 129. In the present example the plant comprises three separate reactor trains with three first quench zones assigned to the reactor trains. Shutoff devices 131 and 132 are provided in the conduits 121 and 124 both at the entrance to and at the exit from the reactor train.

Via conduit 121 and through an entrance-side shutoff device 131 an oxygenates-containing reactant stream is introduced into the OTO reaction zone 111. In this specific case said zone comprises for example three catalyst fixed beds 111a, 111b and 111c filled with solid, granular, shape-selective, commercially available zeolite catalyst but this is to be understood as being merely symbolic of any desired number of catalyst fixed beds. The introduction of additional cooler reactant stream onto every downstream fixed bed is indicated by conduits 141 and 142.

Since operation of the OTO reactor at the lowest possible pressures improves the propylene yield, the pressure drop over the plants, pipelines and other components such as for example valves arranged downstream of the reactor is more important for propylene yield than the pressure drop over corresponding components upstream of the OTO reactor. Thus the more markedly the pressure drop over the plant part between the exit from the OTO reaction zone and the entrance to the compressor can be reduced, the more advantageous this is for the yield of the target products, for example propylene.

In one embodiment of an OTO synthesis plant according to FIG. 1 on an industrial scale the yearly capacity is typically 470 kta of propylene. The volume flow of the product gas at the exit from the OTO reaction zone is 230 kNm³/h at a temperature of 480° C. and a pressure of 130 kPa(a). After exiting the thermal recovery apparatus the product mixture enters a first quench zone in which process water cools the gaseous product mixture having a starting pressure of 118 kPa(a) to 55° C., thus also causing condensation of considerable amounts of water.

Altogether the combination of lower temperature and condensation reduces the actual volume flow from 495 km³/h at the exit from the MTP reactor to 76 km³/h at the exit from the first quenching apparatus. According to customary methods of pipe measurement the recited flows correspond to pipe/valve diameters of 106 inches at the exit from the OTO reaction zone, 86 inches at the exit from the thermal recovery apparatus and 56 inches at the exit from the first quench zone. Since the trade stocks standard sizes for automatically operated valves in sizes below 60 inches a commercially available automatic valve may therefore be used for the outlet-side shutoff apparatus 132. Such an automatic valve is an operated valve controlled by mechanical means or instrument air which allows at least remote control of valve opening/closing operations via a control system. Valve choice represents a compromise between the size, cost and ability of the valve to prevent leakage when in the closed position after repeated switching cycles. The valves are typically specified according to the desired pressure drop. In addition the pressure drop in the fully open position should be relatively low.

As a reference value for the flow rate of the product gas a gas flow rate of 13 m/s in the shutoff device 132 may be used as a basis for an embodiment according to FIG. 1. For a given valve size the change in pressure drop may be determined from the change in flow rate according to $$(\Delta p_2/\Delta p_1)=(v_2/v1)^2,$$

wherein $p_x$ is the actual gas flow rate upon passing through the opened valve and $\Delta p_x$ is the pressure drop to be established.

An increase from 13 to 16 m/s would for example bring about an increase in the pressure drop over the valve of about 50% which elucidates the critical interdependency between the size of the shutoff device and the aim of minimizing the OTO reactor pressure to achieve high propylene yields.

In order during changing of the operating modes of a reactor train from synthesis operation to regeneration operation to ensure reliable and safe separation of oxygen-containing streams and flammable, hydrocarbon-containing gases it is also possible to arrange two automatic valves in series as shutoff devices. This markedly reduces the leakage rate compared to a single valve. This concept also makes it possible to depressurize the space between the two shutoff devices and/or to fill it with inert gas, optionally also under positive pressure. This ensures that in the case of a leak only inert gas penetrates into the plant and no flammable gas is inadvertently discharged into the environment.

The product gas cooled and partially condensed in the first quench zone is passed to the second quench zone via conduit 124 and the shutoff device 132 arranged in conduit path 124 and complete product conduit 126. Joining via the conduit path 125 shown by way of example is the partial product stream from the parallel reactor train (not shown) which is likewise in synthesis operation while a third parallel reactor train is in regeneration mode and is separated from the two reactor trains in synthesis mode by the shutoff device present in this reactor train.

Carried out in the second quench zone is a further cooling of the complete product gas with water as the quenching medium, wherein now it is especially relatively heavy, high-boiling hydrocarbons that condense and the relatively light, low-boiling hydrocarbons that remain in the gas phase. The latter are passed via conduit 128 to a compressor and subsequently to a multistage workup apparatus for workup of the compressed complete product into a plurality of olefin-containing hydrocarbons fractions (compressor and workup apparatus not shown in the figure). The aqueous quenching medium is discharged from the second quench zone via conduit 127. The heavier hydrocarbons form a separate organic liquid phase and via a conduit (not shown) are likewise supplied to the compressor and the downstream workup apparatus. The heavier hydrocarbons may alternatively also be collected in a benzine product without further workup.

Figure 2:
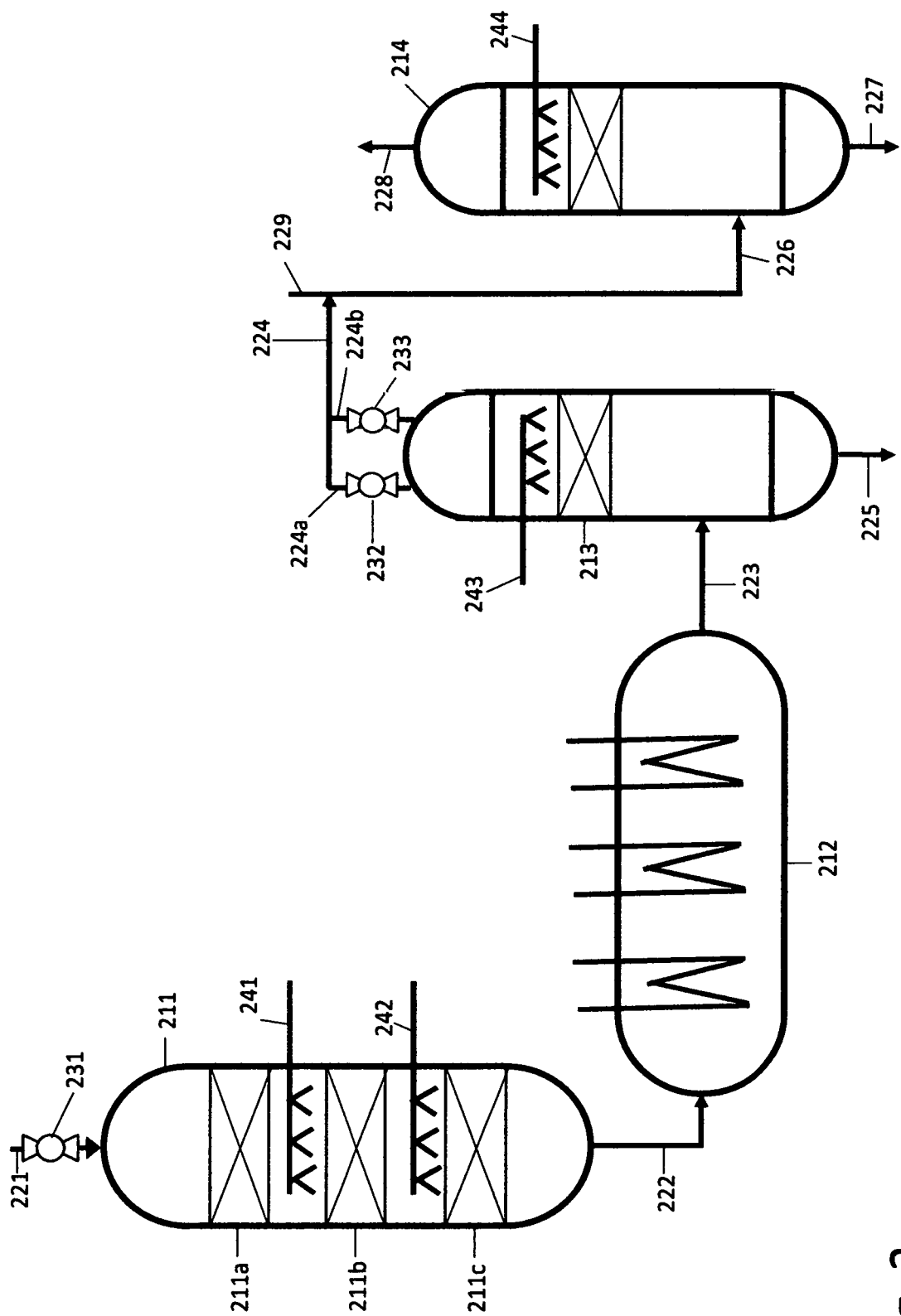
FIG. 2 shows a schematic representation of a second embodiment.

FIG. 2 shows a second embodiment of the present invention. The product mixture discharged from the OTO reaction zone 211 is passed via conduit 222 into a thermal recovery apparatus 212 preferably comprising a plurality of heat exchangers. Subsequently conduit 223 passes the cooled partial product stream into a first quench zone 213 into which the quenching medium, preferably water, is introduced via conduit 243.

From this first quenching apparatus 213 the spent quenching medium is discharged via conduit 225 and the cooled product mixture is passed through two parallel conduits 224a and 224b and the accompanying two shutoff devices 232 and 233, preferably in the form of valves, before it is then discharged via conduit 224 and via conduit 229 combined with streams from other reactor trains arranged in parallel to afford a complete product stream and via conduit 226 introduced into the second quench zone. In said zone a liquid fraction is discharged via conduit 227 and a gaseous fraction is discharged via conduit 228. The quenching medium, preferably water, is introduced via conduit 244 as shown. The further properties and the further workup of the various product streams from the second quench zone correspond to those elucidated in connection with FIG. 1.

The division of the discharge stream from the first quench zone 213 over two shutoff devices arranged in parallel has the result that the size of these two apparatuses, preferably the size of two valves, may be markedly reduced. Thus if valves are used the size thereof may be reduced from about 56 inches to 40 inches. The costs and the leakage rate of two 40 inch automatic valves are markedly reduced compared to 56 inch valves, wherein the pressure drop tends to be reduced and in the worst case remains the same due to the division over two substreams and the accompanying reduction in flow rate. Accordingly this embodiment affords advantages in respect of plant safety and capital costs coupled with identical or improved propylene yield.

Figure 3:
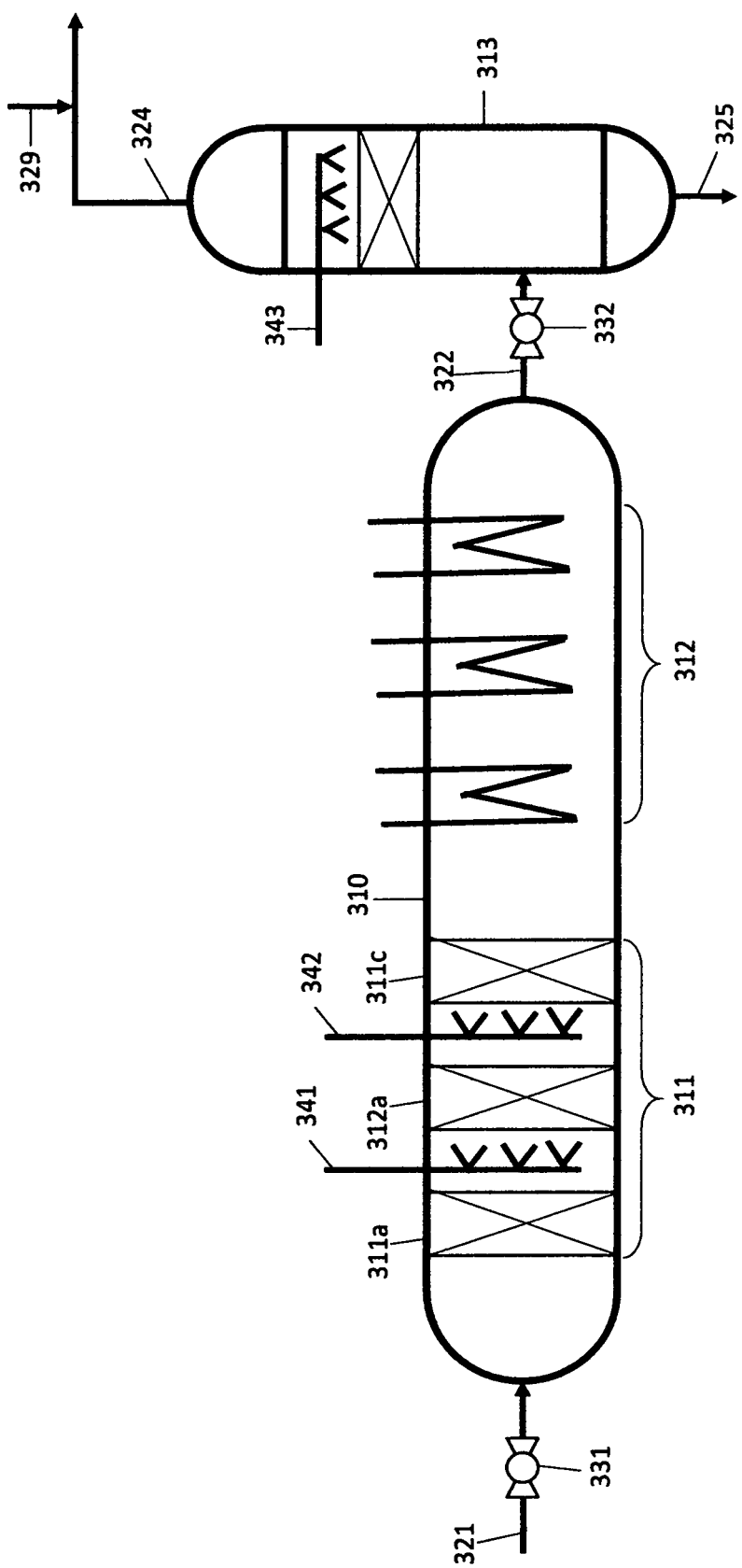
FIG. 3 shows a schematic representation of a third embodiment.

FIG. 3 shows a third embodiment of the invention. Contained here inside a common vessel 310 is a reaction zone 311 and a downstream thermal recovery apparatus 312. Via conduit 321 and the entrance-side shutoff device 331 integrated into its conduit path the reactant substream is introduced into the common vessel 310 where it first passes through the reaction zone 311. Here too, said zone comprises for example three catalyst fixed beds 311a, 311b and 311c. The introduction of additional cooler reactant stream onto every downstream catalyst fixed bed is in turn indicated by the conduits 341 and 342.

The partial product stream discharged from the reaction zone is then passed into a thermal recovery apparatus 312 inside the common vessel 310. The cooled partial product stream then exits the common vessel 310 via conduit 322 and passes through the second shutoff device 332 before—together with the partial product streams from the parallel reactor trains not shown—being introduced into the first quench zone 313 which is supplied with the quenching medium, preferably water, via conduit 343. From this quench zone the gaseous fraction and the liquid fraction are withdrawn via the conduits 324 and 325. The further properties and the further workup of the various product streams from the quench zone correspond to those elucidated in connection with the second quench zone in FIG. 1. Connection to the further reactor trains operated in parallel is in turn indicated by conduit 329.

In this example the reactor train comprises only the reaction zone and the thermal recovery apparatus inside the common vessel. This arrangement generally requires only one common quench system for all parallel reactor trains. Such a configuration is particularly advantageous for example in the following examples:

(a) The partial product stream exiting the reaction zone is cooled to a temperature of about 70° C. using the thermal recovery apparatus through steam generation, methanol evaporation, hydrocarbon recycling evaporation/superheating and/or other process or useful streams. In this case through partial condensation the cooled partial product stream exiting the common vessel 310 is reduced from 330 km³/h at 190° C. before the condensation to only 67 km³/h after the partial condensation of the vapours present through cooling, this corresponding approximately to a mole fraction of 73 mol % (liquid outlet from vessel 310 after cooling not shown). This makes it possible to use relatively customary valve sizes, for example 54 inch, for the shutoff device even for large plant sizes.

(b) The size of the synthesis plant is reduced from 470 kta to a production capacity of 100 kta. In this case the partial product stream exiting the common vessel 310 reduces by a factor of x 100/470 from 330 km³/h to 70 km³/h at 190° C. The valve size requirements likewise fall.

(c) A further option is the reduction of plant capacity from 470 kta to an intermediate size of 200 kta. In this case the partial product stream exiting the reaction zone must be cooled to 90° C. using the thermal recovery apparatus through steam generation, methanol evaporation, hydrocarbon recycling evaporation/superheating and/or other process or useful streams to condense about 39% of the vapours (on a molar basis). The remaining gas volume flow after partial condensation of the vapours present of 67 km³/h then once again makes it possible to utilize commercially available valve sizes, in particular 54 inch.

Figure 4:
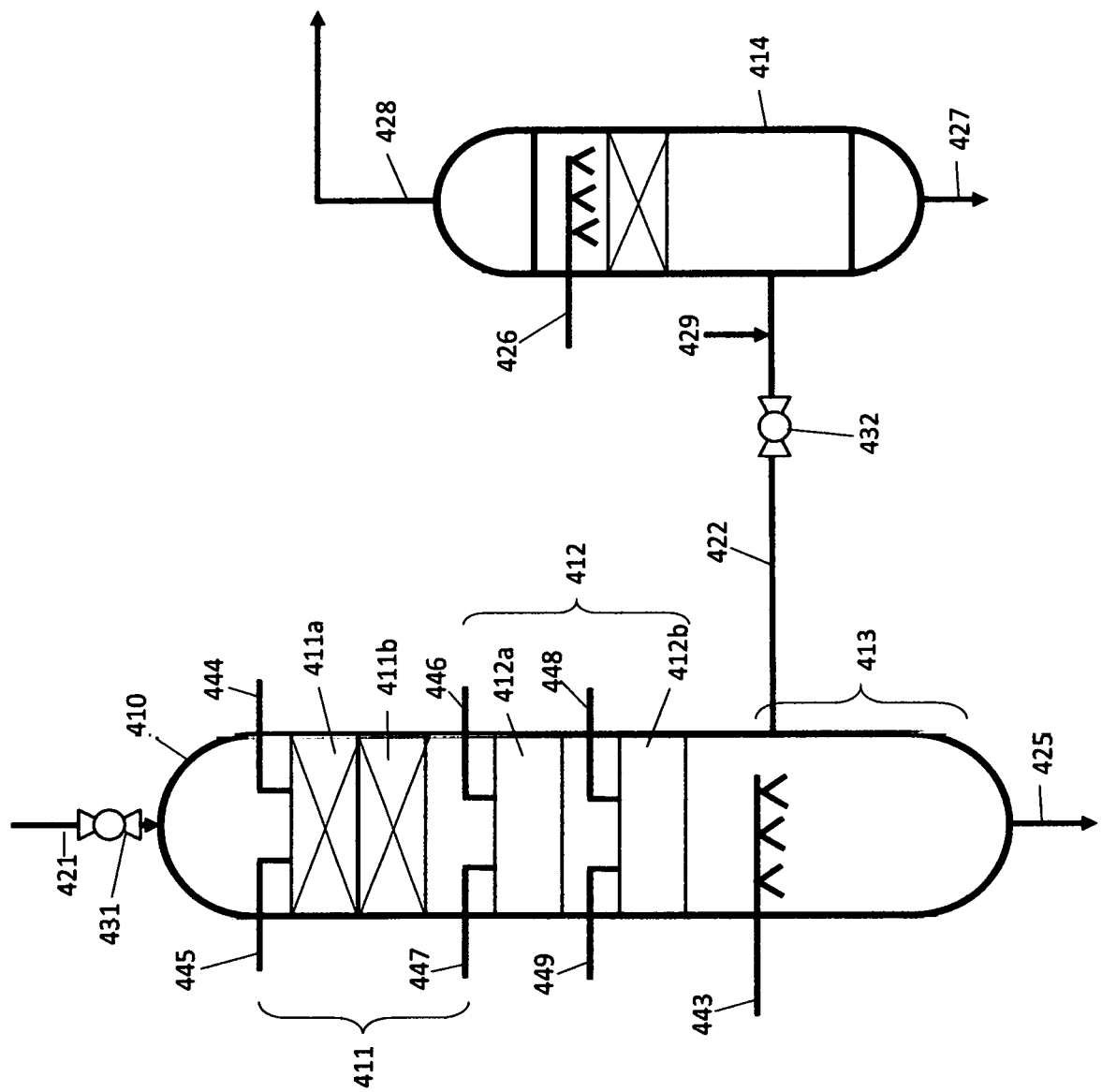
FIG. 4 shows a schematic representation of a fourth embodiment.
Figure 5:
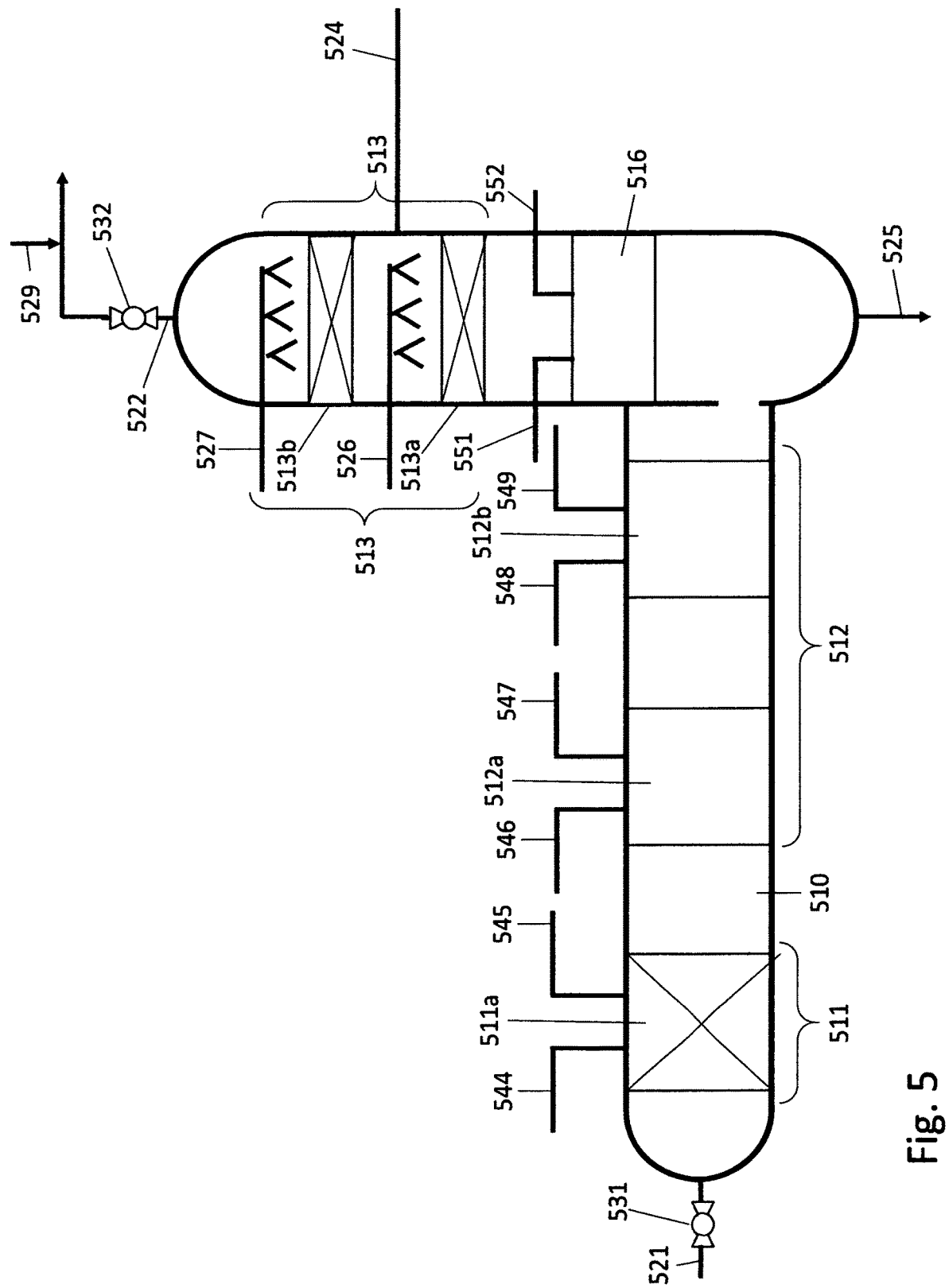
FIG. 5 shows a schematic representation of a fifth embodiment, in each case of the plant according to the invention/of the process according to the invention, wherein the pictorial representation is limited to the plant part/process part downstream of the compressor. In each of the embodiments shown the compressor and the multi-stage workup apparatus downstream of the compressor for separation of the compressed complete product into a plurality of olefin-containing hydrocarbon fractions follow in each case.

In all embodiments of the invention having a common vessel for a plurality of plant parts, i.e. in the exemplary embodiments shown in FIGS. 3, 4 and 5, it is possible to combine this aspect with the division of the partial product stream over two shutoff devices arranged in parallel as shown in FIG. 2.

The main advantage of this embodiment according to FIG. 3 is that the pressure drop between the reaction zone and the thermal recovery apparatus is further minimized compared to the embodiments shown in FIGS. 1 and 2 since conduits between these two assemblies are omitted.

One embodiment of the invention according to FIG. 3 exhibits marked pressure drop reductions compared to the embodiment according to FIG. 1. Thus the pressure drop for the connecting conduit 123 between the reaction zone and the thermal recovery apparatus is 1.2 mbar and the pressure drop over the thermal recovery apparatus is 2.7 mbar, therefore making 3.9 mbar in total. The same arrangement according to FIG. 3 results in a pressure drop of 1.4 mbar and the pressure drop saving is thus 2.5 mbar, corresponding to a pressure drop reduction of 63% compared to an embodiment according to FIG. 1. This corresponds to an improvement in the propylene yield of 1.2% on a relative basis. Applied to a plant capacity of 470 kta this means that for a constant reactant input the propylene production may be increased by 5.8 kta.

The horizontal arrangement of the common vessel 310 shown in FIG. 3 is to be understood as being only exemplary. Depending on the site of installation and the available space a vertical, upright arrangement of the common vessel 310 would also be conceivable and in some cases advantageous.

FIG. 4 shows a fourth embodiment of the present invention. Now also present inside the common vessel 410 in addition to the reaction zone 411 and the thermal recovery apparatus 412 is a first quench zone 413.

By way of example the reaction zone here comprises the two catalyst fixed beds 411a, 411b which are cooled using plate heat exchangers into which a cooling fluid is introduced/discharged via conduits 444, 445. In this way the liberated reaction heat of the exothermic OTO synthesis reactions may be efficiently removed. Any other configuration of the reaction zone is also possible.

Arranged downstream of the reaction zone is the thermal recovery apparatus 412 comprising for example two heat exchangers 412a and 412b which are preferably likewise configured as plate heat exchangers and comprise the feed and discharge conduits 446, 447, 448 and 449 for their respective cooling fluid.

Also arranged downstream of the thermal recovery apparatus in the common vessel 410 is the first quench zone 413 into which the quenching medium is introduced via conduit 443. The first quench zone is preferably operated such that a large part of the water present in the partial product stream may be separated and discharged via conduit 425. Arranged in the conduit 422 is a shutoff device 432 by means of which the cooled and partially condensed product stream is discharged from the reactor train. Via conduit 422 the partial product stream is introduced into a second quench zone 414 together with the partial product streams from the parallel reactor trains not shown in the figure. From this quench zone the gaseous fraction and the liquid fraction are withdrawn via the conduits 428 and 427. The further properties and the further workup of the various product streams from the quench zone correspond to those elucidated in connection with the second quench zone in FIG. 1.

In this embodiment of the invention the reactor train comprises the reaction zone, the thermal recovery apparatus and the first quench zone inside the common vessel. Such a configuration is particularly advantageous for example in the following examples:

(a) The partial product stream exiting the reaction zone is initially cooled by indirect heat exchange using the thermal recovery apparatus, wherein the removed heat is used for steam generation, methanol evaporation, hydrocarbon recycling evaporation/superheating and/or for heating other process or useful streams. A further cooling by direct heat exchange to a temperature of about 70° C. is then effected in the first quench zone. In this case the gas stream is reduced by the partial condensation from 330 km³/h at 190° C. before the condensation to only 67 km³/h after the partial condensation of the vapours present. This corresponds to a condensation of the vapour of about 73 mol % which has the result that even plants having a production capacity of 470 kta may employ customary valves, in particular in a 54 inch size, and the backpressure-mediated pressure drop is correspondingly reduced by the proportion of the removed volume flow.

(b) The size of the synthesis plant is reduced from 470 kta to 120 kta. In this case after passing through the thermal recovery apparatus the stream is proportionally around 330 km³/h×120/470=84 km³/h at 190° C. Passing through the first quench zone causes the gas temperature to fall further from 190° C. to below 100° C. corresponding to a gas volume flow of 70 km³/h. The advantages described for case (a) also apply here.

Integration of reaction zone, thermal recovery apparatus and first quench zone in a common vessel further reduces the pressure drop compared to the examples elucidated hereinabove. In particular, one embodiment of the invention according to FIG. 4 exhibits further marked pressure drop reductions compared to the embodiment according to FIG. 1. Thus the pressure drop for the connecting conduit 123 between the reaction zone and the thermal recovery apparatus is 1.2 mbar and the pressure drop over the thermal recovery apparatus is 2.7 mbar, therefore making 3.9 mbar in total. Furthermore, the first quench zone in FIG. 1 exhibits a pressure drop of 11.2 mbar and 8.4 mbar in the feed and discharge piping respectively. Starting from this cumulative pressure drop of altogether 23.6 mbar the embodiment according to FIG. 4 saves altogether 22.3 mbar, thus corresponding to a reduction of 94%. Such a reduction in pressure drop results in an increase in propylene yield of 3.8% for a constant reactant input which corresponds to an additional yield of 17.9 kta of propylene for a plant capacity of 470 kta.

FIG. 5 finally shows a fifth embodiment of the present invention. It comprises the arrangement of the reaction zone 511, the thermal recovery apparatus 512 and the quench zone 513 configured as a double quench comprising the first quench zone 513a and the second quench zone 513b in a common vessel 510.

Via conduit 521 and the entrance-side shutoff device 531 integrated into its conduit path the reactant substream is introduced into the common vessel 510 where it first passes through the reaction zone 511. By way of example the reaction zone here comprises the catalyst fixed bed 511a which is cooled using a plate heat exchanger into which a cooling fluid is introduced/discharged via conduits 544, 545. In this way the liberated reaction heat of the exothermic OTO synthesis reactions may be efficiently removed. Any other embodiment of the reaction zone is possible. It is preferable when the reaction zone comprises a plurality of catalyst fixed beds arranged in series.

Arranged downstream of the reaction zone is the thermal recovery apparatus 512 comprising for example two heat exchangers 512a and 512b which are preferably likewise configured as plate heat exchangers and comprise the feed and discharge conduits 546, 547, 548 and 549 for their respective cooling fluid. This is followed by a change in the flow direction of preferably 90°, wherein—depending on the conditions at the site of installation—an embodiment without a change or with a different change in flow direction is also conceivable. However, the depicted upright arrangement of the plant part downstream of the heat exchanger 512b is advantageous since condensates and quenching media accumulate here to a greater extent and are therefore easier to collect and discharge via conduit 525.

In this specific case a further heat exchanger 516 having accompanying feed and discharge conduits 551 and 552 for the cooling medium and also attributable to the thermal recovery apparatus 512 is employed. This heat exchanger 516 may alternatively be provided at another location or not at all.

The cooled reaction mixture subsequently passes through the quench system 513 comprising the first quench zone 513a and the second quench zone 513b which are supplied with quenching medium via conduits 526 and 527 respectively. One or more liquid phases are withdrawn via conduit 525 and optionally also conduit 524. The conduit 524 shown in the figure is to be understood as being merely exemplary and variable in terms of its height of arrangement. If a second liquid phase is to be withdrawn via conduit 524 it is advantageous to provide between the first and the second quench zone a separating tray not shown in the figure, for example a chimney tray, which is permeable to the gas phase but impermeable to the second liquid phase so that said phase collects on the separating tray and may be discharged via conduit 524.

The gaseous fraction is discharged via conduit 522 and the shutoff device 532 arranged in conduit path 522. The joining of the partial product streams from further reactor trains operated in parallel is again indicated symbolically via conduit 529. The further properties and the further workup of the various product streams from the quench zone correspond to those elucidated in connection with the second quench zone in FIG. 1.

In this embodiment of the invention the reactor train comprises the reaction zone, the thermal recovery apparatus and both quench zones inside the common vessel. Such a configuration is particularly advantageous for example in the following examples:

(a) The partial product stream exiting the reaction zone is initially cooled to an intermediate temperature of 100° C. to 160° C. by indirect heat exchange using the thermal recovery apparatus before condensation of the liquid is carried out. The gas temperature is subsequently reduced to below the condensation point using additional heat exchangers, for example the heat exchanger 516. It is advantageous here when due to the arrangement of the heat exchanger 516 in the vertical part of the common vessel the condensate produced can flow away in a downward direction, thus allowing it to be discharged via conduit 525 together with the spent quenching medium. A further cooling to a temperature of about 70° C. is then carried out by direct heat exchange in the first quench zone.

This is followed by a further temperature reduction to a temperature of 50° C. to 95° C. in the first quench zone and finally to a temperature of 40° C. to 50° C. in the second quench zone. In this example the partial condensation reduces the partial product gas stream from 330 km³/h (based on a plant capacity of 470 kta) at 190° C. before the cooling and condensation to only 48 km³/h which corresponds to a condensation of 79 mol % of the vapour which has the result that even plants having a production capacity of 470 kta may employ customary valves, in particular in a 45 inch size, and the backpressure-mediated pressure drop is correspondingly reduced by the proportion of the removed volume flow.

(b) In a development of the example elucidated at (a) the partial product volume flow was reduced to 42 km³/h when an exit temperature of 40° C. and thus a condensation of 81 mol % of the vapour were achieved. This would even allow valve sizes of 42 inches. Here too it is possible to combine this aspect with the division of the partial product stream over two shutoff devices arranged in parallel as shown in FIG. 2, thus making it possible to use valve sizes of 30 or 32 inches.

Integration of reaction zone, thermal recovery apparatus and both quench zones in a common vessel still further reduces the pressure drop compared to the examples elucidated hereinabove. In particular, one embodiment of the invention according to FIG. 5 exhibits a further pressure drop reduction of 9.3 mbar compared to the embodiment according to FIG. 4 and the total pressure drop of 32.8 mbar (reaction zone, thermal recovery apparatus and both quench zones each in separate vessels with connecting conduits) can therefore be reduced by altogether 31.5 mbar, i.e. by 96%. This brings about an increase in propylene yield of 4.8% which corresponds to an increase of 22.6 kta for a plant capacity of 470 kta.

LIST OF REFERENCE NUMERALS 111 reaction zone
111a-111c catalyst fixed bed
112 thermal recovery apparatus
113 first quench zone
114 second quench zone
121-129 conduit
131, 132 shutoff device
141-144 conduit
211 reaction zone
211a-211c catalyst fixed bed
212 thermal recovery apparatus
213 first quench zone
214 second quench zone
221-229 conduit
231-233 shutoff device
241-244 conduit
310 common vessel
311 reaction zone
311a-311c catalyst fixed bed
312 thermal recovery apparatus
313 first quench zone
321-329 conduit
331, 332 shutoff device
341-343 conduit
410 common vessel
411 reaction zone
411a-411b catalyst fixed bed with heat exchangers
412 thermal recovery apparatus
412a-412b heat exchanger
413 first quench zone
414 second quench zone
421-429 conduit
431, 432 shutoff device
443-449 conduit
510 common vessel
511 reaction zone
511a catalyst fixed bed with heat exchanger
512 thermal recovery apparatus
512a, 512b heat exchanger
513 quench system
513a first quenching apparatus
513b second quenching apparatus
521-529 conduit
531, 532 shutoff device
544-552 conduit

What is claimed is:

1. A multi-strand plant for producing olefins from an oxygenates-containing fluid input mixture comprising the following constituents and assemblies in fluid connection with one another:
   (a) at least two reactor trains arranged in parallel and operable in parallel, wherein each reactor train comprises:
      (a1) at least one oxygenate-to-olefin reaction zone containing a catalyst active and selective for the conversion of the oxygenates into olefins under oxygenate conversion conditions, a means for supplying the oxygenates-containing input mixture to the reaction zone, a means for discharging an olefins-containing partial product stream from the reaction zone, a means for supplying a gaseous oxygen-containing regenerant to the reaction zone, and a means for discharging a carbon oxides-containing regeneration offgas from the reaction zone,
      (a2) a thermal recovery apparatus arranged downstream of the reaction zone comprising at least one heat exchanger for performing indirect heat exchange between the product gas discharged from the reaction zone and a cooling fluid,
      (a3) a partial product conduit arranged downstream of the thermal recovery apparatus for discharging the partial product stream from the reactor train,
      (a4) a shutoff device in the conduit path of the partial product conduit for separating a reactor train from downstream plant parts and parallel reactor trains,
   (b) a connecting device arranged downstream of the individual reactor trains for combining the individual partial product conduits into a complete product conduit,
   (c) a compressor arranged downstream of the connecting device for compressing the complete product supplied using the complete product conduit,
   (d) a multi-stage workup apparatus arranged downstream of the compressor for separating the compressed complete product into a plurality of olefin-containing hydrocarbon fractions,
   (e) wherein furthermore at least one first quench zone for performing direct heat exchange between one or more partial product streams or the complete product stream and a first quenching medium is comprised, wherein the first quench zone is arranged downstream of the thermal recovery apparatus and upstream of the compressor.

2. The plant according to claim 1, wherein arranged in every reactor train downstream of the thermal recovery apparatus are at least two partial product conduits for discharging the partial product stream from the reactor train which are arranged in parallel and operable in parallel, and wherein at least one shutoff device is present in the conduit path of each of the parallel partial product conduits.

3. The plant according to claim 1, wherein a first quench zone for performing direct heat exchange between a partial product stream and a first quenching medium is comprised and is arranged downstream of the thermal recovery apparatus and upstream of the connecting device and in that a second quench zone for performing direct heat exchange between the complete product stream and a second quenching medium is further comprised and is arranged downstream of the connecting device and upstream of the compressor and is in fluid connection with all partial product conduits from the individual reactor trains.

4. The plant according to claim 3, wherein the first quench zone is arranged downstream of the thermal recovery apparatus and upstream of the shutoff device.

5. The plant according to claim 1, wherein the at least one reaction zone and the thermal recovery apparatus arranged downstream of the reaction zone are arranged in a common vessel, and wherein the partial product conduit arranged downstream of the thermal recovery apparatus is used to discharge the partial product stream from the vessel.

6. The plant according to claim 1, wherein:
the at least one reaction zone and the thermal recovery apparatus arranged downstream of the reaction zone are arranged in a common vessel,
the partial product stream is discharged from the vessel using the partial product conduit arranged downstream of the thermal recovery apparatus,
all partial product conduits of the reactor trains are combined using the connecting device,
the first quench zone is arranged between the connecting device and the compressor and is in fluid connection with all partial product conduits of the individual reactor trains.

7. The plant according to claim 1, wherein:
the at least one reaction zone, the thermal recovery apparatus arranged downstream of the reaction zone and the first quench zone arranged downstream of the thermal recovery apparatus are arranged in a common vessel,
the partial product stream is discharged from the vessel using the partial product conduit arranged downstream of the first quench zone,
all partial product conduits of the reactor trains are combined using the connecting device, and
the second quench zone is arranged between the connecting device and the compressor and is in fluid connection with all partial product conduits of the individual reactor trains.

8. The plant according to claim 1, wherein:
the at least one reaction zone, the thermal recovery apparatus arranged downstream of the reaction zone, the first quench zone arranged downstream of the thermal recovery apparatus and the second quench zone arranged downstream of the first quench zone are arranged in a common vessel, and
the partial product stream is discharged from the vessel using the partial product conduit arranged downstream of the second quench zone,
all partial product conduits of the reactor trains are combined using the connecting device.

9. The plant according to claim 5, wherein the common vessel is connected to a conduit for discharging a liquid condensate.

10. The plant according to claim 5, wherein the thermal recovery apparatuses are in the form of plate heat exchangers.

11. The plant according to claim 10, wherein the thermal recovery apparatuses comprise at least two plate heat exchangers operated with different cooling fluids.

12. The plant according to claim 5, wherein the reaction zones are in a heat transfer relationship with plate heat exchangers by means of which the reaction zones are cooled with a cooling fluid by indirect heat exchange.

13. A process for producing olefins from an oxygenates-containing fluid input mixture comprising the following steps:
(a) providing the oxygenates-containing fluid input mixture,
(b) supplying the oxygenates-containing fluid input mixture to a plant according to claim 1, and converting the input mixture into olefin-containing partial product streams under oxygenate conversion conditions,
(c) discharging at least one olefin-containing hydrocarbon fraction from the plant, wherein
the plant comprises at least two reactor trains arranged in parallel and operable in parallel, of which
at least one reactor train is supplied with oxygenates-containing, fluid input mixture, wherein the obtained partial product stream is discharged from the reactor train and via the opened shutoff device and the connecting device is supplied to the workup apparatus and in parallel therewith
at least one further reactor train is supplied with a gaseous oxygen-containing regenerant, wherein a carbon oxides-containing regeneration offgas is obtained which is discharged from the reactor train and wherein the shutoff device of this reactor train is closed.

14. The process according to claim 13, wherein the plant comprises three reactor trains, of which two are supplied with oxygenates-containing, fluid input mixture and in parallel thereto one is supplied with a gaseous oxygen-containing regenerant.

15. The process according to claim 13, wherein at least 40 of the product gas is separated as condensate upstream of the shutoff apparatus.

* * * * *